United States Patent [19]

Wyslouzil

[11] 4,193,027
[45] Mar. 11, 1980

[54] MICROWAVE MOISTURE-PROFILE GAUGE

[75] Inventor: Walter Wyslouzil, Carlsbad Springs, Canada

[73] Assignee: Canadian Patents and Development Limited, Ottawa, Canada

[21] Appl. No.: 947,889

[22] Filed: Oct. 2, 1978

[51] Int. Cl.² .......................................... G01R 27/04
[52] U.S. Cl. .................................... 324/58.5 R
[58] Field of Search ............... 324/58.5 A, 58.5 R, 324/58 A, 58 R, 58.5 B

[56] References Cited

U.S. PATENT DOCUMENTS

| | | | |
|---|---|---|---|
| 3,470,343 | 9/1969 | Bilbrough | 324/58.5 A |
| 3,534,260 | 10/1970 | Walker | 324/58.5 A |

Primary Examiner—Rudolph V. Rolinec
Assistant Examiner—Ernest F. Karlsen
Attorney, Agent, or Firm—Edward Rymek

[57] ABSTRACT

The scanning microwave detection apparatus provides a moisture profile along the width of a predetermined sample such as a sheet or web. The apparatus includes a number of moisture sensors spaced along the width of the sample, such that each sensor couples microwave energy with a finite area of the sample. Each sensor is preferably a pair of horns with one located on each side of the sample to provide a microwave path through the sample. A first filter is coupled to the input of each sensor and a second filter is coupled to the output of each sensor. The pair of filters associated with each sensor is tuned to the same frequency, and each of the pairs of filters are tuned to a different predetermined frequency within a selected frequency band such that the sensors operate at different frequencies, within substantially non-overlapping frequency band-passes. The filters are preferably directional. A microwave source is coupled to the input filters and is controlled to sweep through the selected frequency band to sequentially energize each sensor. A detector is coupled to the output filters for detecting the sequential energy outputs of the sensors. These sequential outputs are a function of the moisture content of the finite areas of the sample at the sensors.

3 Claims, 3 Drawing Figures

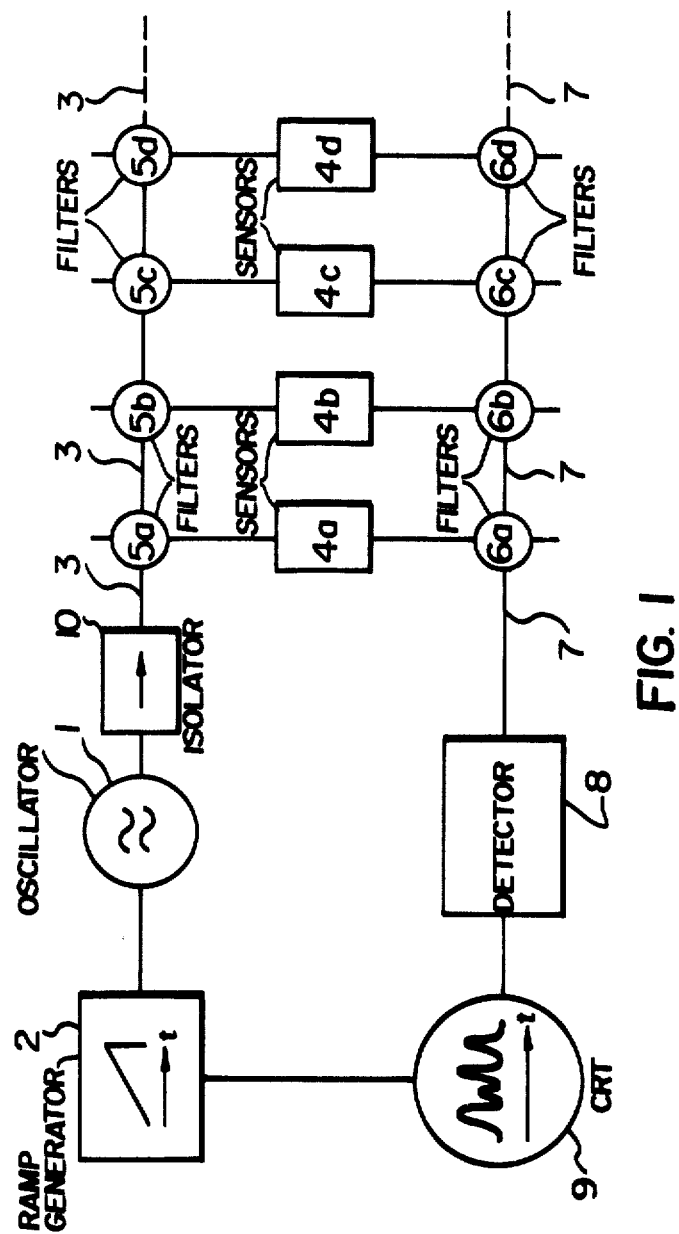
FIG. I

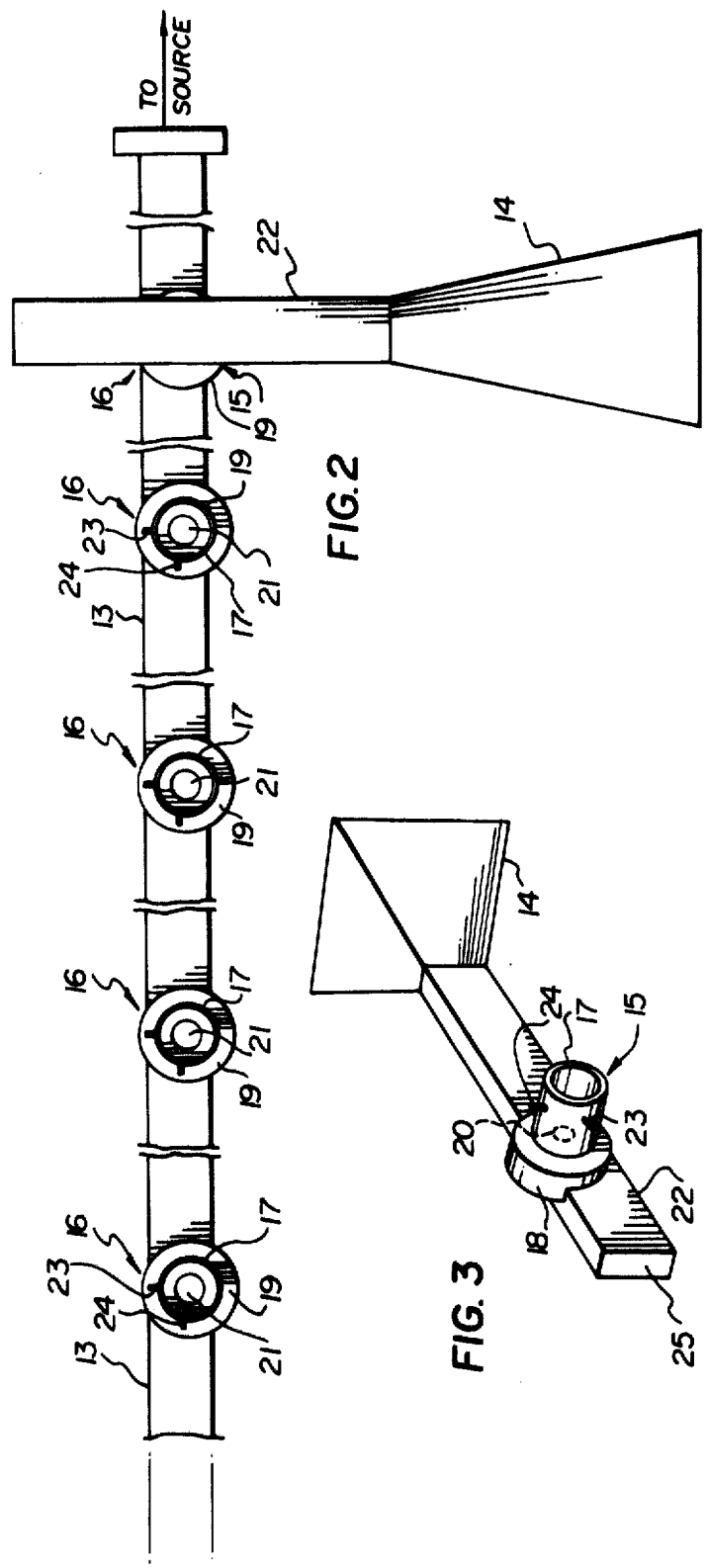

MICROWAVE MOISTURE-PROFILE GAUGE

BACKGROUND OF THE INVENTION

This invention is directed to a moisture detection apparatus for sheets or webs and in particular to a scanning microwave moisture detection apparatus for providing a moisture profile of the sheet or web.

In order to control paper making machines, it is desirable to determine the moisture content of the paper at various stages of the process. To achieve this, either fixed or scanning microwave moisture detectors are used to detect the moisture content of the sheet or web which is moving at a speed from a hundred feet per minute to several thousand feet per minute. One type of sensor which may be used for this purpose includes a fringing field sensing head which is in contact with one side of the sheet. The fringing field interacts with the sheet and microwave power is absorbed. Thus the attenuation of the power in the sensing head is a function of the moisture in the sheet. Another type of sensor includes a transmitter horn on one side of the sheet and a receiver horn on the other side. This is a non-contacting sensor and some of the microwave power transmitted through the sheet will be absorbed by the moisture in the sheet. Thus the power received by the receiver horn is a function of the moisture content of the sheet.

In many instances it is highly desirable to scan the sheet or web along its width and obtain a moisture profile of the sheet. The prior art teaches two types of scanning systems, one being mechanical and the other using electronic switching. In the mechanical system, which is the only one that is in common use, the sensor is physically moved across the width of the sheet. This need for moving parts results in a rather combersome apparatus and provides a profile which varies with the direction of travel of the sheet or web. In the electronic system, as described in U.S. Pat. No. 3,534,260, Oct. 13, 1970, C. W. E. Walker, power is switched from one sensor to the next, requiring an elaborate control system. In U.S. Pat. No. 3,470,343, Sept. 30, 1969, J. Bilbrough, both mechanical scanning and electronic sampling of the output from an array of separate moisture gauges is described.

SUMMARY OF THE INVENTION

It is therefore an object of this invention to provide a scanning microwave moisture detection system for measuring the moisture profile of a sheet or web.

This and other objects are achieved in a detection apparatus which includes a predetermined number of moisture sensors that are spaced so as to be positioned across the width of the sheet or web sample such that when energized, each of the sensors couples microwave energy with a finite area of the sample. A first filter is coupled to the input of each sensor and a second filter is coupled to the output of each sensor. The pair of filters associated with a particular sensor is tuned to the same frequency and each of the pairs of filters are tuned to a different predetermined frequency within a selected frequency band, such that the sensors operate at predetermined different frequencies within substantially non-overlapping frequency band-passes. A microwave source is coupled to the input filters, and is controlled to sweep the selected frequency band to sequentially energize each sensor. A detector is coupled to the output filters for detecting the sequential energy outputs of the sensors, these outputs are a function of the moisture content of the sample at each sensor.

Each of the sensors consists of a first horn coupled to the first filter for transmitting microwave energy and a second horn coupled to the second filter for receiving microwave energy, the first and second horns are positioned on opposite sides of the sample to provide a microwave path through the sample which absorbs microwave energy in proportion to its moisture content. In addition, the filters are directional filters to minimize signal losses and to substantially prevent reflection.

BRIEF DESCRIPTION OF THE DRAWINGS

In the drawings:

FIG. 1 schematically illustrates the scanning microwave moisture detection apparatus;

FIG. 2 illustrates the arrangement of the microwave transmitting or receiving horns on a waveguide; and FIG. 3 illustrates the structure of the directional filters for each of the transmitting and receiving horns.

DESCRIPTION OF THE PREFERRED EMBODIMENTS

A microwave moisture detection system in accordance with the present invention is illustrates in FIG. 1. The system consists of a variable frquency oscillator 1 which is controlled by a ramp voltage generator 2 or some other conventional means to provide an output that is swept in frequency. The oscillator is coupled via a waveguide 3 to a number of sensors $4a$, $4b$, $4c$, $4d$, . . . . These sensors are designed to couple to a sheet or web in which the moisture level is to be measured. In order to have each sensor respond to a particular frequency, a filter $5a$, $5b$, $5c$, $5d$, . . . is located between the input waveguide 3 and each sensor $4a$, $4b$, $4c$, $4d$, . . . . In order to completely isolate each sensor and its response, a further directional filter $6a$, $6b$, $6c$, $6d$, . . . is located between each sensor $4a$, $4b$, $4c$, $4d$, . . . and an output waveguide 7. Each of the filter pairs $5a$–$6a$, $5b$–$6b$, $5c$–$6c$, $5d$–$6d$, . . . are tuned to a different frequency in a predetermined frequency band and have substantially non-overlapping band-passes.

The output is detected on waveguide 7 by a detector 8 which provides a sequential output proportional to the microwave energy passed through the individual sensors $4a$, $4b$, $4c$, $4d$, . . . . Since in coupling with the sheet or web, the amount of energy absorbed by the web is directly proportional to the moisture content of the area of the sample coupled, the output detected by detector 8 will be inversely proportional to the moisture content, i.e. the detected output at detector 8 will decrease with increase in moisture content.

The output of detector 8 may be recorded on a CRT display 9 or any other conventional means. The output may alternately be used by a computer to directly control the manufacture of the sample. In addition, display 9 may be coupled to ramp-generator 2 to synchronize the display 9 with the frequency sweep. Finally, an isolator 10 may be included in the microwave circuit between oscillator 1 and waveguide 3 to isolate the oscillator from reflections.

In operation, oscillator 1 generates energy at a swept frequency. Sensors $4a$, $4b$, $4c$, $4d$, . . . are energized individually in succession as a result of the selected band pass of filters $5a$, $5b$, $5c$, $5d$, . . . . Energy in respective sensors $4a$, $4b$, $4c$, $4d$, . . . is absorbed by an amount dependent on the moisture in the area of the sheet or web near the sensor. The remaining energy from each successive sensor 4a, 4b, 4c, 4d, . . . is transferred to output waveguide 7 via filters 6a, 6b, 6c, 6d, . . . where it is detected as successive pulses as shown on display 9. Band-pass filters 6a, 6b, 6c, 6d, . . . effectively isolate the sensors from one another and also assure that essentially all of the received signal is coupled to the detector 8.

FIGS. 2 and 3 illustrate the preferred embodiment for waveguides 3 and 7, filters 5a, 5b, 5c, 5d, . . . and 6a, 6b, 6c, 6d, . . . , and sensors 4a, 4b, 4c, 4d, . . . which each consist of two horns, one located on each side of the sheet or web to be tested such that one horn transmits energy through the sheet or web where it is received by the second horn. The transmitting section of the waveguide, filters, and sensors, is identical to the receiving section.

In particular, waveguide 13 is a standard WR42 waveguide with 0.5"×0.25" outside diameter and having 0.040" walls for operation in the K-band. A number of spaced predetermined locations 16 on the waveguide 13 are selected for coupling to a filter 15 and the sensor horn 14. The number of sensors will dpend on the width of the sheet or web to be measured and the desired spacing between sensors. Typically, the testing of a 400" sheet would be carried out by a system of 60 sensors.

The filter 15 consists of a cylindrical cavity as shown in FIGS. 2 and 3. The cavity includes a cylinder 17, having an inside diameter of 0.4" and a 0.05" wall thickness, which is capped by recessed disks 18 and 19. The disks 18 and 19 have centered coupling holes 20 and 21 respectively and are fixed to a waveguide 22 and waveguide 13 respectively. In order to achieve directionality, the cavity coupling holes 20 and 21 are offset to one side of the waveguides 22 and 13 respectively. The mid-frequency of filters 15 is dependent on the length of the cylinder 17 with fine tuning being accomplished by tuning screws 23 and 24, while the bandwidth is dependent on the size of the coupling holes 20 and 21. Directional filters are described in the text, "Microwave Filters, Impedance-Matching Networks, and Coupling Structures" by Matthei, Young, Jones; McGraw-Hill, 1964, pp 847–859. Waveguide 22 is terminated at one end preferably by a matched load 25 and at the other end by the horn 14.

The above system is particularly advantageous in the determination of the moisture profile of a sheet or web since moving parts are not necessary in the scanning of the sheet and the construction of the microwave components is straight forward. In addition, since a particular frequency corresponds to the center frequency of one pair of filters, almost all of the signal is coupled to the transmitting horn and almost all of the signal reaching the receiving horn is coupled to the detector maintaining losses at a minimum. Also, since adjacent transmission paths in the array operate at different frequencies, there is no cross-coupling between adjacent horns.

I claim:

1. A scanning microwave detection apparatus for providing a moisture profile along the width of a predetermined sample, comprising:
   a plurality of spaced moisture sensors, each of the sensors adapted to couple microwave energy with a finite area of the sample;
   each sensor having a first filter coupled to its input and a second filter coupled to its output, the first and second filters forming a pair, the pair of filters coupled to each sensor being tuned to the same frequency and each of the pairs of filters being tuned to a different predetermined frequency within a selected frequency band thereby having a substantially non-overlapping frequency band-pass;
   microwave source controlled to sweep through the frequencies within the selected frequency band, said source being coupled to the input filters; and
   detector means coupled to the output filters for sequentially detecting energy outputs of the sensors which are a function of the moisture content of the sample.

2. An apparatus as claimed in claim 1 wherein each of the sensors consists of a first horn coupled to the first filter for transmitting microwave energy and a second horn coupled to the second filter for receiving microwave energy, the first and second horns being adapted to be positioned on opposite sides of the sample to provide a microwave path through the sample.

3. An apparatus as claimed in claim 2 wherein the filters are directional filters.

* * * * *